United States Patent [19]

Baumoel

[11] Patent Number: 4,467,659
[45] Date of Patent: Aug. 28, 1984

[54] TRANSDUCER HAVING METAL HOUSING AND EMPLOYING MODE CONVERSION

[76] Inventor: Joseph Baumoel, 107 Columbia Dr., Jericho, N.Y. 11753

[21] Appl. No.: 407,434

[22] Filed: Aug. 12, 1982

[51] Int. Cl.³ .............................................. G01F 1/66
[52] U.S. Cl. .................................. 73/861.27; 73/644; 310/366
[58] Field of Search ...................... 73/642, 644, 861.18, 73/861.27, 861.28; 310/334, 335, 336; 367/150, 151

[56] References Cited

U.S. PATENT DOCUMENTS

| 3,050,997 | 4/1962 | Lake. | |
| 3,869,915 | 3/1975 | Baumoel | 73/861.28 |
| 3,987,674 | 10/1976 | Baumoel | 73/861.28 |

*Primary Examiner*—Herbert Goldstein
*Attorney, Agent, or Firm*—Ostrolenk, Faber, Gerb & Soffen

[57] ABSTRACT

A pair of transducers each having metal housings are clamped at spaced axial locations along a conduit and transmit ultrasonic signals to one another through the fluid within the conduit. The difference in upstream and downstream transit times for the ultrasonic energy is used to determine the flow velocity and other characteristics of the fluid within the conduit. Each of the transducer housings has the shape of a trapezohedron, one surface of which converts longitudinal mode sonic energy from a transducer crystal into reflected shear mode sonic energy which is applied at an angle to the pipe surface. The phase velocity of the shear mode sonic energy of the transducer housing matches the shear mode sonic energy in the conduit wall so that there is extremely close coupling between the housing and the conduit and energy is transmitted through the conduit interior over a long axial length of the conduit.

14 Claims, 7 Drawing Figures

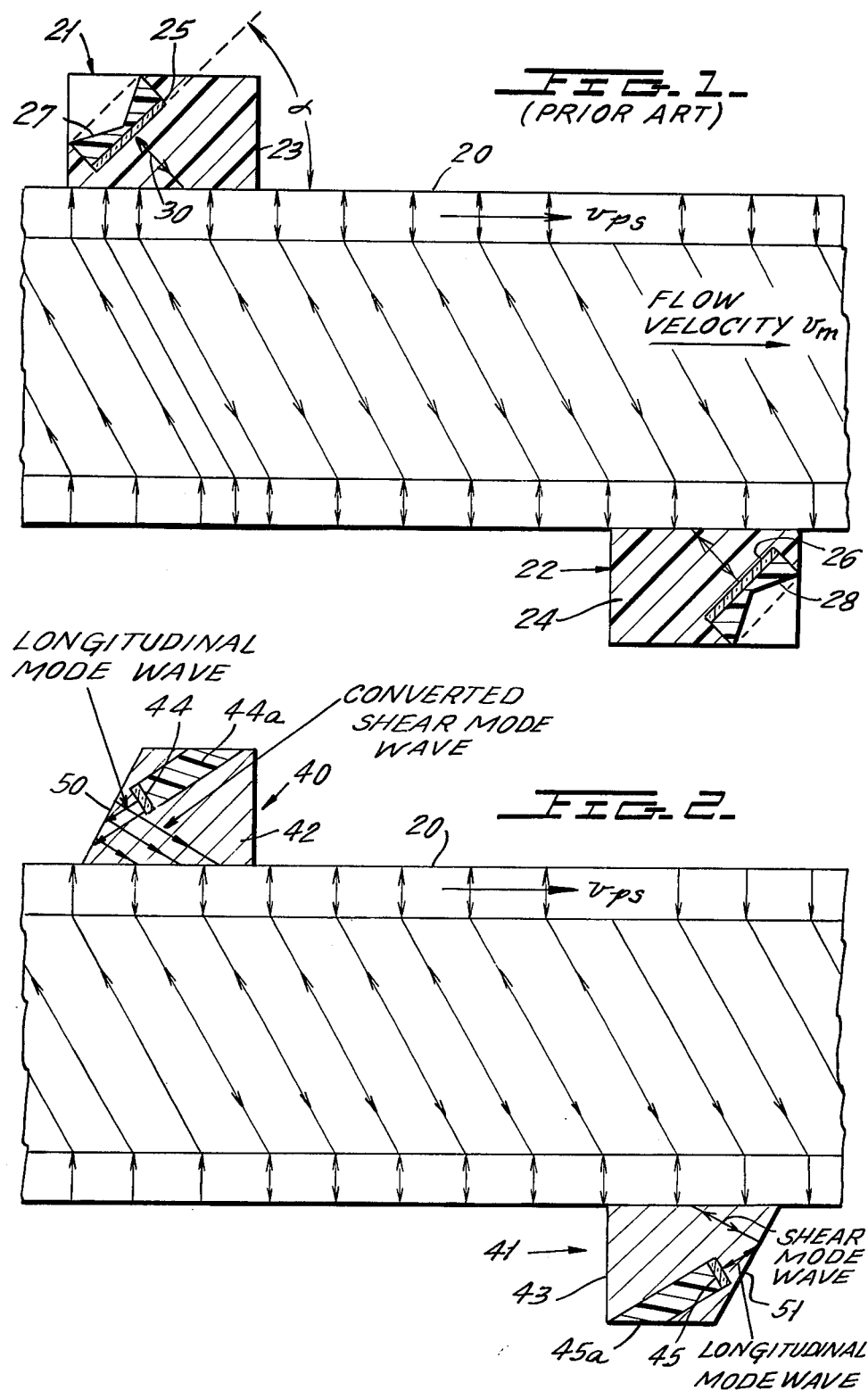

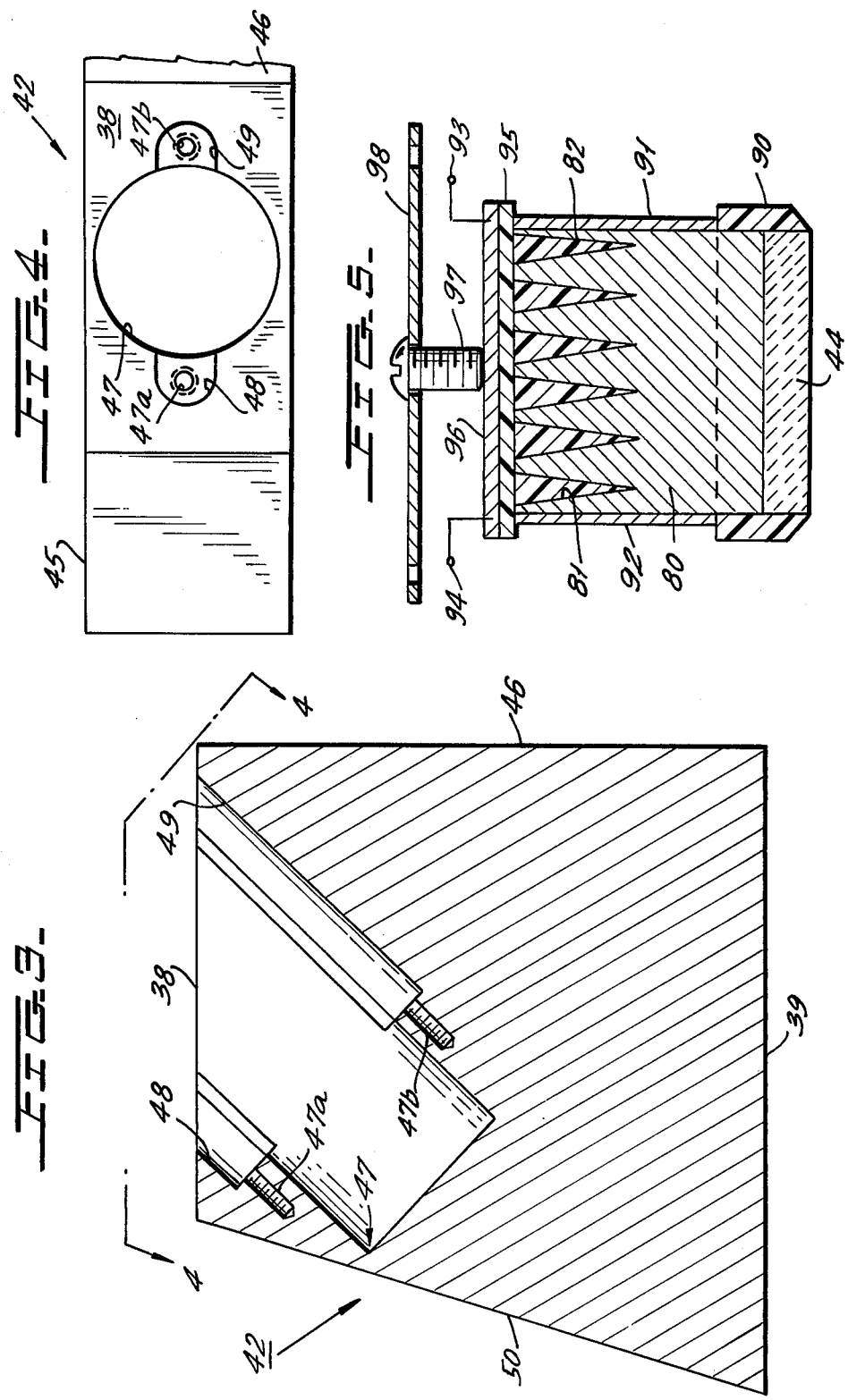

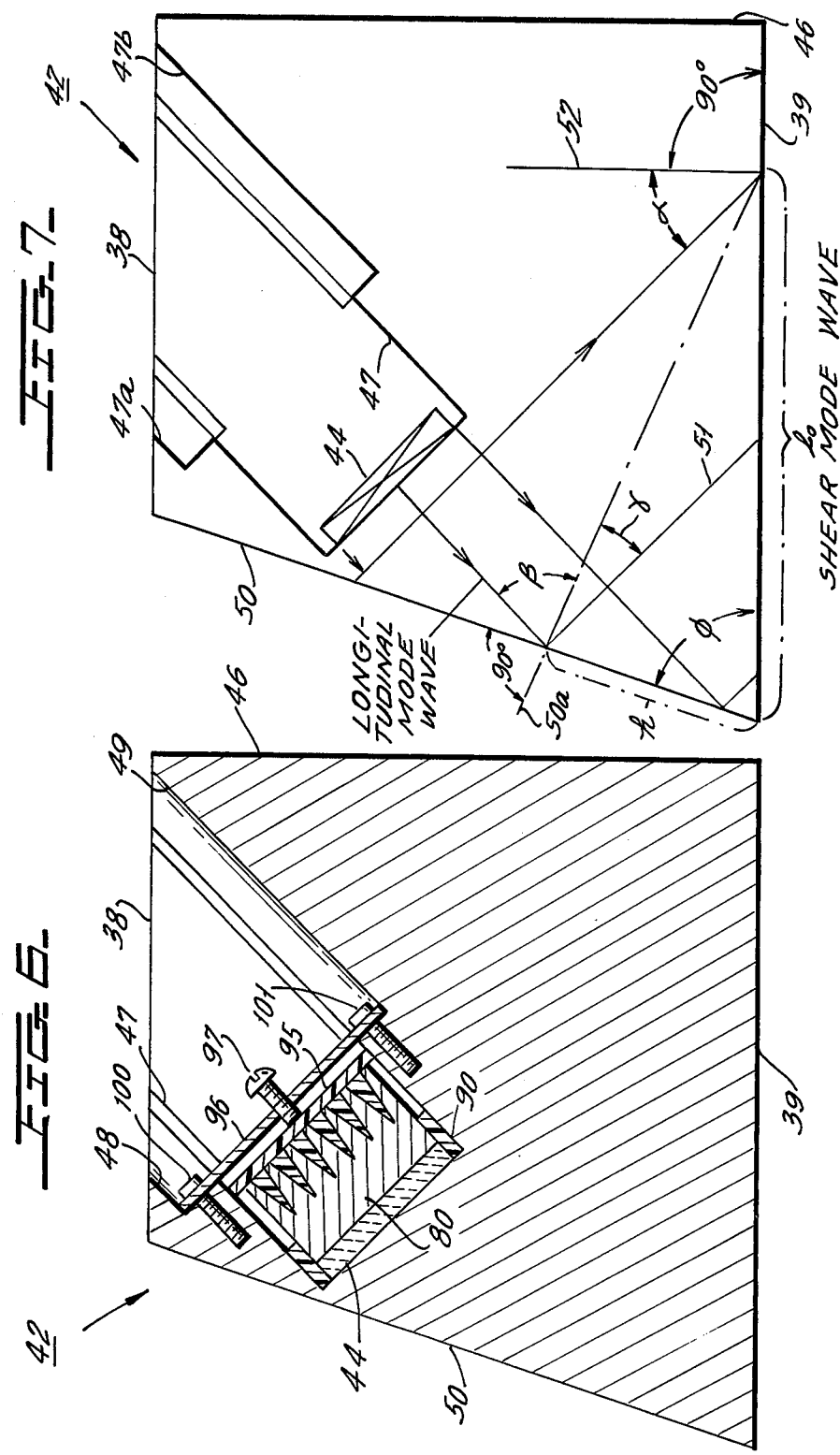

1

TRANSDUCER HAVING METAL HOUSING AND EMPLOYING MODE CONVERSION

BACKGROUND OF THE INVENTION

This invention relates to transducers for flow monitoring equipment and more particularly relates to a transducer employing mode conversion for a flow monitoring application.

Transducer structures for flow monitoring equipment are known and are shown, for example, in U.S. Pat. Nos. 3,869,915 and 3,987,674, each of which is in the name of Joseph Baumoel. Transducer structures for such flowmeters are also shown in copending application Ser. No. 146,530, filed May 5, 1980 in the name of Joseph Baumoel, now U.S. Pat. No. 4,373,401.

The above patents and application disclose a transducer system in which ultrasonic energy is injected into a conduit over a relatively long axial distance of the conduit so that the receiving transducer can receive a usable signal without having to be at an exact axial location relative to the transmitting transducer. This is done by causing a shear mode sonic wave to propagate along the pipe wall in response to a longitudinal mode sonic wave in the transducer housing. Thus, the longitudinal wave from the transducer housing is applied at an agle to the pipe axis so that the phase velocity of the longitudinal transducer housing wave arriving at the pipe surface is equal to the pipe shear wave velocity. In particular, the sine of the angle between the transducer crystal and the pipe surface is made equal to the ratio of the longitudinal mode sonic velocity of the housing to the shear mode velocity of the conduit. This produces good coupling between the transducer housing and the pipe housing and introduces considerable energy along the axis of the pipe to produce what is known as a large "footprint".

In order to carry out this concept, it is necessary that the longitudinal mode sonic velocity of the transducer housing be less than the shear mode sonic velocity of the pipe or conduit. This is required since the phase velocity of the longitudinal wave must be increased to the shear wave velocity in the pipe wall. Because of this requirement, when the conduit is made of metal such as steel, which has a high shear wave velocity of approximately $126 \times 10^3$ inches/second, the transducer body had to be of a non-metallic material having a longitudinal sonic velocity less than that of the metal pipe.

This has prevented the use of metal transducer housings in the past and required the use of materials such as plastics for the transducer housing. Plastics, however, are generally limited in their operating temperature range so that the system described above was limited to relatively low temperature applications or required the use of esoteric and expensive plastics such as polyimid amides. Thus, while it was desirable to employ metallic transducer housings which have very stable temperature characteristics, metal transducer housings have not been used, prior to this invention, because their longitudinal mode sonic velocity is higher than the shear mode velocity of a metal conduit.

A principal object of this invention is to provide a novel arrangement which permits metals such as brass, zinc, copper and the like to be used for the transducer body of an ultrasonic measuring system in which the transducers are clamped directly to the conduits or pipes which carry fluid, the characteristics of which are to be measured or determined, which conduits may be of ferrous or other metal material and which may be at very high temperature.

BRIEF DESCRIPTION OF THE INVENTION

In accordance with the invention, a novel metallic transducer housing is provided which has a shape which converts an injected longitudinal sonic energy beam from a transducer crystal into a shear mode beam by internal reflection from a surface of the housing. It is known that a longitudinal wave form can be converted, by internal reflection at a suitable angle, into a wave having both a longitudinal mode and a shear mode. This phenomenon is known as "mode conversion". It is also known that substantially all longitudinal mode energy can be converted into shear mode energy when the angle of incidence of the longitudinal mode energy relative to a normal to the reflecting surface is appropriately chosen and if the material has a Poisson's ratio of about 0.26.

The transducer housing is arranged so that the shear mode wave which has been converted from the longitudinal mode input energy is directed at the surface of a pipe at an angle such that the phase velocity of the shear mode wave in the housing equals the shear mode velocity of the conduit. By phase velocity is meant the conventional concept of the velocity of a point which moves with a wave at constant phase. Thus, there will be excellent coupling between a metal transducer housing and the metallic pipe.

By way of example, metals such as zinc and brass can be employed for the transducer housing. Zinc has a Poisson's ratio of approximately 0.26 so that virtually all energy of the longitudinal mode input energy can be converted to shear mode energy which can be applied to the conduit. Brass has a Poisson's ratio of approximately 0.33 but brass is more easily available than zinc and is less expensive than zinc. Thus, while brass is not as efficient as zinc, for the mode conversion phenomenon, the phenomenon still takes place and substantial shear mode wave energy is produced for injection into the pipe wall.

Brass has a longitudinal mode velocity of sound of about $170 \times 10^3$ inches/second. The transducer arrangements shown in the above-listed patents and pending application could not have employed brass (or other metals) for the housing since the longitudinal velocity of sound is greater than the shear mode velocity in a steel pipe or conduit which is about $126 \times 10^3$ inches/second. Thus, the shear mode wave in the metal conduit could not be excited from the higher speed longitudinal mode wave in the housing. The shear mode wave velocity in brass, however, is only about $80 \times 10^3$ inches/second which is substantially less than the shear mode velocity in a steel pipe. One can therefore inject the shear mode velocity at an angle to the axis of the pipe conduit so that the phase velocity of the shear mode wave which reaches the conduit surface equals the shear mode velocity of the pipe. Consequently, there is excellent coupling of energy to the pipe with the use of a metal transducer housing.

Note that the novel invention is not limited to applications for metal conduits and metal housings but, more broadly, is concerned with the production of a transducer housing which employs mode conversion in order to produce a shear mode beam for injection into a conduit wherein the shear mode velocity of the transducer housing material is lower than the shear mode velocity of the conduit. Commonly, however, the invention is applicable to metallic conduits such as those of iron and steel which can now employ a metallic transducer housing having relatively low cost and high temperature stability.

BRIEF DESCRIPTION OF THE DRAWINGS

FIG. 1 shows a transducer system of the prior art type.

FIG. 2 shows a novel transducer system which employs transducers constructed in accordance with the present invention.

FIG. 3 is a cross-sectional view of a metallic transducer housing of trapezohedron shape and constructed in accordance with the present invention.

FIG. 4 is a view of FIG. 3 as seen from the line 4—4 in FIG. 3.

FIG. 5 is a cross-sectional view of a damper and crystal assembly which can be assembled with the housing of FIGS. 3 and 4.

FIG. 6 shows the assembly of the housing of FIGS. 3 and 4 and the damper and transducer crystal subassembly of FIG. 5.

FIG. 7 is a schematic view of FIG. 6 and contains notations useful in explaining the operation of the invention.

DETAILED DESCRIPTION OF THE DRAWINGS

Referring first to FIG. 1, there is shown therein the prior art arrangement of transducers in a system of the type such as that shown in U.S. Pat. No. 3,987,674. In this system, it is desired to measure the flow velocity of a material such as a liquid within the conduit 20. A pair of transducers 21 and 22 are clamped to the outside surface of the conduit 20 and are axially displaced from one another. A suitable clamping means such as that shown in copending application Ser. No. 146,530 referred to above can be used to secure the transducers to the conduit 20.

Transducers devices 21 and 22 consist of housings 23 and 24, respectively, which contain transducer crystals 25 and 26, respectively. The transducer crystals can be any type of transducer element such as well known single or polycrystalline devices. Crystals 25 and 26 can be excited in the usual manner to produce output sonic pulse trains which propagate through housings 23 and 24 with longitudinal mode transmission. The rear surfaces of transducer crystals 25 and 26 are preferably provided with dampers 27 and 28, respectively, as described in U.S. Pat. No. 3,987,674 or as will be described hereinafter.

Transducer assemblies 21 and 22 alternate as transmitters and receivers, respectively, of ultrasonic energy. Initially, for example, transducer assembly 21 is the transmitter. Crystal 25 injects a longitudinal mode wave into housing 23, which propagates toward the pipe or conduit 20 to excite a shear mode wave in the wall of the conduit. Energy from the conduit wall enters the fluid or other contents within pipe 20 and passes through the pipe interior. The transmitted pulse is ultimately received by transducer crystal 26. A suitable electronic conduit (not shown) measures the transit time of the signal through the interior of conduit 20. Crystal 26 then returns a similar sonic signal which is received by the crystal 25 and the transit time is measured. The times for upstream and downstream transmission of the signals are then subtracted to produce a measure of the flow velocity of the fluid within the conduit 20.

The "footprint" of the sonic signal which is transmitted through the interior of conduit 20 is extremely long, as shown in FIG. 1. Thus, the axial location of the transducer assemblies 21 and 22 relative to one another is noncritical. This long footprint is obtained by adjusting the angle α of FIG. 1 such that the wave front of the longitudinal mode wave traveling parallel to line 30 reaches the wall of the conduit 20 at an angle such that the phase velocity of the longitudinal mode wave equals the shear mode velocity $V_{ps}$ in the pipe or conduit wall 20. As a result, the shear mode wave propagates axially along the wall of pipe 20 and acts as a new source of coherent signals which are introduced into the interior of conduit 20 and arrive, ultimately, at the receiving transducer location.

This wide beam arrangement has made possible extremely sensitive, yet rugged transducer systems which can be clamped to the exterior of a conduit without having to critically locate the transducers relative to one another or to adjust their positions relative to one another as temperature changes or as the conduit contents change. Moreover, the same transducer can be used for a wide variety of pipe materials and diameters. It is, however, necessary to choose materials for transducer bodies 23 and 24 of FIG. 1 which have longitudinal mode sonic velocities which are less than the shear mode velocity $V_{ps}$ of the conduit material. This is necessary so that the phase velocity of the sonic energy in the housings 23 and 24 can be adjusted to match the shear mode velocity of the pipe.

The material of conduit or pipe 20 is commonly steel. The shear mode velocity of steel is $126 \times 10^3$ inches/second. Thus, the material used for transducer housings 23 and 24 must have a longitudinal mode velocity substantially less than $126 \times 10^3$ inches/second. Since metals commonly have a longitudinal mode sonic velocity much higher than $126 \times 10^3$ inches/second, it has been necessary to use plastic materials for the transducer body. Common plastic materials, however, are not stable over wide temperature ranges and therefore cannot be used, for example, on steel pipe carrying hot fluids so that esoteric, expensive plastics are needed for these applications.

The present invention provides a novel structure and process for injecting a relatively low shear mode velocity sonic wave from a transducer housing, which preferably but not necessarily of metal, into a pipe wall which is preferably but not necessarily metal.

More particularly and as shown in FIG. 2, mode conversion transducer assemblies 40 and 41 are clamped to the surface of conduit 20. The mode conversion transducer assemblies 40 and 41 consist of housings 42 and 43, respectively, which have the shape of a trapezohedron. The bodies 42 and 43 receive transducer crystals 44 and 45, respectively, which may be backed by suitable dampers 44a and 45a, respectively. Dampers, however, are not needed. Moreover, the crystals 44 and 45 can be placed on the top surface of their housing bodies 42 and 43, with these surfaces at an appropriate angle so that the energy of crystals 44 and 45 propagates in the desired direction.

Housings 42 and 43 have respective mode conversion reflection surfaces 50 and 51 which are arranged to receive the longitudinal mode wave output of transducer crystals 44 and 45, respectively, and to reflect a large percentage of this longitudinal mode energy as a shear mode wave which is directed toward and at an angle α to the surface of conduit 20. As will be later described in more detail, the mode conversion transducers 40 and 41 inject a shear mode sonic energy wave into conduit 20 which has a phase velocity equal to the shear mode velocity $V_{ps}$ of the conduit 20 material.

By converting to shear mode energy within the housing 42, one can now select metals for the housing material since the shear mode velocity of metals having a suitable Poisson's ratio for the mode conversion phenomenon to be used will have a lower shear mode velocity than that, for example, of steel. By way of example, housings 42 and 43 may be of brass which has a longitudinal mode velocity of $170 \times 10^3$ inches/second which is too high to be coupled to conduit 20 if it is made of steel. However, the shear mode velocity of brass is only $80 \times 10^3$ inches/second. Consequently, a brass transducer housing can be used in connection with an iron or steel conduit 20 in place of the more esoteric low longitudinal mode velocity plastics which were previously required.

FIGS. 3 and 4 show the novel housing 42 of the present invention in greater detail. The housing may be machined from any desired metal. Zinc has been used successfully. Brass such as brass-CDA 464 which is finished with a nickel plate has been used successfully.

The metal housing of FIGS. 3 and 4 has the general shape of a trapezohedron and has flat parallel top and bottom surfaces 38 and 39, respectively, and non-parallel flat surfaces 50 (FIG. 3) and 46 which complete the trapezoidal outline of the housing. A transducer receiving opening 47 is machined into the top surface 38 and securement bracket openings 48 and 49 having tapped openings 47a and 47b, respectively, at their bases are provided as shown. Note that top surface 38 can directly receive a transducer crystal and, if so, the surface 38 would be sloped to be parallel to the bottom of opening 47. If opening 47 is used, transducer crystal 44 is appropriately seated on the bottom of opening 47 after the bottom of opening 47 has been satinized to ensure very close coupling between the lower surface of crystal 44 and the bottom of opening 47.

The flat surface 50 serves as the mode converting surface which converts a longitudinal mode sonic wave directed at its internal surface into a reflected shear mode wave and vice-versa of opening. The bottom 39 serves as the surface of the transducer which is ultimately coupled to a volume, such as a conduit 20, which is to receive energy from the transducer. Any desired well-known type of transducer element or crystal can be used.

For purposes of illustration, one typical brass transducer housing, which was built and tested and which employed the concept of the present invention, had a width of about 1.6", a length for surface 46 of about 4.37", a length for surface 39 of about 4.81" and a length for surface 38 of about 3.5". In order to ensure conversion from the longitudinal mode wave to the shear mode wave, and as shown in FIG. 7, the angle β between the axis of opening 47 and a normal 50a to surface 50 is made to be 65°. This, in combination with a Poisson's ratio of the brass, ensures conversion of a substantial portion of the longitudinal energy into shear mode energy. The shear mode energy then propagates in the direction of line 51 of FIG. 7 which is at an angle γ to the normal 50a which is 25.25°. Note that the angle α between the normal 52 to the direction of travel of the shear mode wave is 43.60°. The ultimate relationships between the various dimensions are determined by the following equations:

$$\sin \gamma = (v_{cs}/v_{cl}) \sin \beta \qquad (1)$$

$$\sin \alpha = (v_{cs}/v_{ps}) \qquad (2)$$

$$\phi = \alpha + \gamma \qquad (3)$$

$$h = (d/\cos \beta) \qquad (4)$$

$$l_o = (h \cos \gamma / \cos \alpha) = (d \cos \gamma / \cos \beta \cos \alpha) \qquad (5)$$

In the above equations:

$v_{cs}$ is the shear mode velocity of the transducer body 42;

$v_{cl}$ is the longitudinal mode velocity of transducer body 42;

$v_{ps}$ is the shear mode velocity of the conduit to which the transducer is connected;

h is the distance along face 50 from the bottom of the face to the point where the axis of opening 47 intersects the face;

$l_o$ is the length along the bottom surface 39 at which energy is injected into the pipe or conduit;

d is the diameter of the transducer crystal 44.

The transducer crystal 44 is shown in FIGS. 2, 5, 6 and 7 as secured to the bottom of a suitable damper and mounting support structure. The damper and mounting support structure of FIG. 5 for the crystal is the body which holds the crystal in place within the transducer housing and also receives and damps rearward-going energy put out from the rear surface of the transducer crystal. The damper can be eliminated from the design when using a metal housing.

If a damper is used, it should be very closely coupled to the rear surface of the transducer crystal 44 so that energy can flow freely into the damper. Thereafter, however, the energy should be dissipated and attenuated and the coherency of the beam should be interrupted to the largest degree possible. As pointed out in copending application Ser. No. 146,530, referred to above, an effective damper was produced of an epoxy body having suspended therein metal particles and other plastic particles which served as scattering centers and attenuated energy which entered the damper. In addition, a single conical opening was provided which served as a reflection surface to increase the path length of the sonic energy within the damper to ensure a greater opportunity to attenuate the wave by the suspended particles in the damper.

The damper body may be made of metal such as brass, lead, zinc or the like wherein a plurality of tapered or conical openings are formed in the rear reflecting surface of the damper. These openings are filled with a plastic having good sonic attenuation characteristics. As a result, sonic energy can freely enter the damper but it experiences multiple non-coherent reflections by the numerous conical opening walls. The energy which enters the material within the conical openings is then severely attenuated, thus producing effective damping. Such a damper makes it possible to put out a pulse from the transducer which is extremely sharp and well defined and does not have a "ringing" characteristic.

The preferred form of the damper is shown in FIG. 5 wherein the brass body 80 has a large plurality of conically tapered openings such as openings 81 and 82 therein which are packed as closely together as reasonably possible. The conical openings 81 and 82 have apices which form an angle of about 19° and any suitable length.

After machining and otherwise processing the damper structure 80, the conical openings 81 and 82 are filled with an epoxy having immersed therein small metal and plastic particles which serve as additional scattering centers, as shown in FIG. 5. A plastic ring 90 is then cemented to the outer periphery of crystal 44 and to the bottom outer periphery of damper 80 in order to secure the two together. A suitable coupling grease can be employed between the surfaces of crystal 44 and damper 80.

The face contact of crystal 44 is electrically connected by means (not shown) to the lead 91. Similarly, the rear electrode of crystal 44 is connected by means (not shown) to lead 92. Leads 91 and 92 are then connected to electrically accessible terminals 93 and 94, respectively, which are connected to the transducer driving and receiving circuits.

The top of damper 80 then receives a gasket 95 which is covered by a pressure disk 96. The pressure disk 96 is adapted to receive a pressure screw 97 which is threaded through support plate 98 which is bolted in place as shown in FIG. 6 by the bolts 100 and 101 which secure the assembly of FIG. 5 within the opening 47 in the housing 42.

In operation, and as shown in FIG. 6, when an electrical pulse is applied to terminals 93 and 94 of transducer crystal 44, the transducer puts out a high frequency longitudinal mode pulse. This longitudinal wave is injected into housing 42 and is intercepted by the interior wall of mode conversion surface 50. As shown in FIG. 7, the energy reflected from mode conversion surface 50 is at an angle $\gamma$ to the normal 50a and is in the form of a shear mode wave which has a velocity substantially less than the velocity of the longitudinal mode wave produced by crystal 44. This shear mode wave then exits along the length $l_o$ of surface 39 and enters the wall of the pipe 20 (FIG. 2) with a phase velocity which is matched to the shear mode velocity of sonic energy in the pipe wall material. Consequently, there is an excellent impedance match between the transducer and the pipe so that there is maximum energy transfer with very sharp pulse signals being applied to the pipe wall and into the interior of the conduit.

The back-reflected signals of transducer crystal 44 are well absorbed and attenuated by the damper assembly shown in FIGS. 5 and 6. Thus, reflected signals are not introduced into the circuit which would interfere with the sensing of a precise point within the main transmit pulse.

Although the present invention has been described in connection with a plurality of preferred embodiments thereof, many variations and modifications will now become apparent to those skilled in the art. It is preferred, therefore, that the present invention be limited not by the specific disclosure herein, but only by the appended claims.

What is claimed is:

1. The process of applying ultrasonic energy to a metal conduit carrying a fluid; said conduit having a characteristic shear mode velocity for sonic energy which propagates axially along said conduit; said process comprising producing longitudinal mode sonic energy wave in a metallic transducer housing which is clamped to the exterior of said conduit; converting said longitudinal mode sonic energy wave into shear mode energy wave by internal reflection of said longitudinal mode sonic energy wave from a surface of said metallic transducer housing; and applying said shear mode sonic energy wave to said metal conduit; the angle of travel of said shear mode sonic energy wave relative to the axis of the conduit being such that the phase velocity of said shear mode sonic energy wave in said housing as it reaches the surface of said conduit equals the said shear mode velocity in said conduit.

2. The process of measuring the flow velocity of a fluid in a conduit by injecting an ultrasonic wave into the interior of a metal conduit which carries a fluid in order to measure the flow of said fluid; said conduit having a characteristic shear mode velocity for sonic energy which propagates axially along said conduit; said process comprising producing longitudinal mode sonic energy wave in a metallic transducer housing; converting said longitudinal mode sonic energy wave into shear mode energy wave, by internal reflection of said longitudinal mode sonic energy wave from a surface of said metallic transducer housing; and applying said shear mode sonic energy from said transducer housing to the outer surface of said metal conduit; the angle of travel of said shear mode sonic energy wave relative to the axis of said conduit being such that the phase velocity of said shear mode sonic energy wave in said housing as it reaches the surface of said conduit equals the said shear mode velocity in said conduit.

3. The process of claim 2 which further includes sensing the time of arrival of said ultrasonic wave at a region axially removed from the region at which it is injected into said conduit.

4. A transducer comprising, in combination, a transducer element and a metal housing having the shape of a trapezohedron; said trapezohedron having a first planar edge surface defining an output energy surface and a second planar edge surface defining a mode conversion surface by internal reflection of a longitudinal mode wave; said first and second planar surfaces intersecting one another with an internal angle $\phi$; said transducer element being a flat, thin element disposed within an opening in said metal housing and disposed in a plane which has a normal which forms an internal angle $\beta$ with respect to a normal to said second planar surface; longitudinal sonic energy from said transducer element being reflected from the interior of said second surface and being converted into shear mode sonic energy which is directed away from said second surface in a direction which forms an internal angle $\gamma$ with respect to a normal to said second planar surface and on the side of said normal away from the side thereof defining said angle $\beta$; wherein $\phi = \alpha + \gamma$; $\alpha$ is the internal angle between the direction of propagation of said shear mode wave and a normal to said first planar surface; and $\sin \gamma = (v_{cs}/v_{cl}) \sin \beta$ wherein $v_{cs}$ is the shear mode velocity of said metal and $v_c$ is the longitudinal mode velocity of said metal; said second surface being coupled to a hollow elongated metal conduit; said metal conduit having a characteristic shear mode velocity $v_{ps}$ and wherein $\sin \alpha = (v_{cs}/v_{ps})$.

5. The transducer of claim 4, wherein said metal housing is of brass.

6. The transducer of claim 4, wherein said metal housing is of zinc.

7. The transducer of claim 4, wherein said conduit is a ferrous metal.

8. A flow monitoring system for measuring the flow in a metal conduit comprising first and second transducers clamped to the exterior of said conduit and axially displaced from one another; each of said transducers comprising, in combination: a transducer element and a metal housing having the shape of a trapezohedron; said trapezohedron having a first planar edge surface defining an output energy surface and a second planar edge surface defining a mode conversion surface by internal reflection of a longitudinal mode wave; said first and second planar surfaces intersecting one another with an internal angle $\phi$; said transducer element being a flat, thin element fixed to said metal housing and disposed in a plane which has a normal which forms an internal angle $\beta$ with respect to a normal to said second planar surface; longitudinal sonic energy from said transducer element being reflected from the interior of said second surface and being converted into shear mode sonic energy which is directed away from said second surface in a direction which forms an internal angle $\gamma$ with respect to a normal to said second planar surface and on the side of said normal away from the side thereof defining said angle $\beta$, wherein $\phi = \alpha + \gamma$; $\alpha$ is the internal angle between the direction of propagation of said shear mode wave and a normal to said first surface; and sin $\gamma = (v_{cs}/v_{cl}) \sin \beta$, wherein $v_{cs}$ is the shear mode velocity of said metal housing and $v_{cl}$ is the longitudinal mode velocity of said metal housing; and electronic means connected to said first and second transducers for measuring the difference in transit time of sonic energy through the fluid in said conduit in the upstream and downstream directions.

9. The system of claim 8, wherein said metal housing is selected from the group consisting of brass, copper and zinc.

10. The system of claim 8, wherein sin $\alpha = (v_{cs}/v_{ps})$ wherein $v_{ps}$ is the shear mode velocity of the metal of said conduit.

11. The system of claim 10, wherein said conduit is of ferrous material.

12. A flow monitoring system for measuring the flow of a fluid in a metal conduit comprising first and second transducers clamped to the exterior of said conduit and axially displaced from one another; each of said transducers comprising a transducer element and a metal transducer housing; said transducer element generating a longitudinal mode sonic energy beam in said housing which has a greater velocity than the shear mode velocity $v_{ps}$ of said conduit; each of said transducer elements including mode conversion surface means intercepting said longitudinal mode sonic energy beam and converting it to a shear mode sonic beam of velocity $v_{cs}$ which is less than said shear mode velocity of said conduit; said shear mode sonic energy beam in said housing forming an angle $\alpha$ to a normal to the axis of said conduit such that sin $\alpha = (v_{cs}v_{ps})$; and electronic means connected to said first and second transducers for measuring the difference in transit time of sonic energy through the fluid in said conduit in the upstream and downstream directions.

13. The system of claim 12, wherein said metal housing is selected from the group consisting of brass, copper and zinc.

14. The system of claim 13, wherein said conduit is of ferrous material.

* * * * *